United States Patent
Gliner

(10) Patent No.: US 10,244,963 B2
(45) Date of Patent: Apr. 2, 2019

(54) ASCERTAINING A POSITION AND ORIENTATION FOR VISUALIZING A TOOL

(71) Applicant: BIOSENSE WEBSTER (ISRAEL) LTD., Yokneam (IL)

(72) Inventor: Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 629 days.

(21) Appl. No.: 14/978,811

(22) Filed: Dec. 22, 2015

(65) Prior Publication Data

US 2017/0172456 A1   Jun. 22, 2017

(51) Int. Cl.
| | |
|---|---|
| A61B 5/00 | (2006.01) |
| A61B 5/06 | (2006.01) |
| A61B 5/055 | (2006.01) |
| A61B 18/14 | (2006.01) |
| A61M 25/01 | (2006.01) |
| A61B 18/00 | (2006.01) |

(52) U.S. Cl.
CPC .............. *A61B 5/066* (2013.01); *A61B 5/055* (2013.01); *A61B 5/064* (2013.01); *A61B 5/6852* (2013.01); *A61B 5/7425* (2013.01); *A61B 18/1492* (2013.01); *A61M 25/0127* (2013.01); *A61B 2018/00351* (2013.01); *A61B 2018/00577* (2013.01); *A61B 2560/0223* (2013.01); *A61B 2576/00* (2013.01)

(58) Field of Classification Search
CPC .......... A61B 5/066; A61B 5/055; A61B 5/064
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,368,285 B1 | 4/2002 | Osadchy et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 7,653,426 B2 | 1/2010 | Yatsuo et al. |

(Continued)

OTHER PUBLICATIONS

European Search Report, Application No./Patent No. 16205689.9-1657, dated May 3, 2017.

*Primary Examiner* — Joel F Brutus
(74) *Attorney, Agent, or Firm* — Notaro, Michalos & Zaccaria P.C.

(57) ABSTRACT

While a catheter that includes (i) a catheter body, and (ii) a catheter shaft, which includes a sensor and which is disposed inside a lumen of the catheter body, is inside a body of a subject, a position and an orientation of a distal end of the catheter body with respect to the sensor are ascertained, based on (a) a calibration image, acquired by an imaging system, that shows an indication of the distal end of the catheter body, and (b) a signal from the sensor, but not based on any indication of the sensor shown in the calibration image. Using the ascertained position and orientation of the distal end of the catheter body with respect to the sensor, a visual output is generated. Other embodiments are also described.

9 Claims, 5 Drawing Sheets

(56) References Cited

U.S. PATENT DOCUMENTS

| | | |
|---|---|---|
| 7,937,132 B2 | 5/2011 | Piron et al. |
| 8,974,460 B2 | 3/2015 | De la Fuente Klein et al. |
| 2004/0077942 A1* | 4/2004 | Hall ........................ A61B 6/12 |
| | | 600/428 |
| 2004/0097805 A1* | 5/2004 | Verard ............... A61B 1/00071 |
| | | 600/428 |
| 2005/0182319 A1 | 8/2005 | Glossop |
| 2007/0049817 A1 | 3/2007 | Preiss |
| 2007/0232882 A1 | 10/2007 | Glossop |
| 2009/0264736 A1* | 10/2009 | Griswold ............... A61B 5/055 |
| | | 600/423 |
| 2011/0230758 A1 | 9/2011 | Eichler |
| 2012/0059249 A1 | 3/2012 | Verard |
| 2012/0105480 A1* | 5/2012 | Barley ................... A61B 90/36 |
| | | 345/641 |
| 2013/0030385 A1* | 1/2013 | Schultz ............. A61B 18/1492 |
| | | 604/247 |
| 2013/0083988 A1 | 4/2013 | Barbot et al. |
| 2014/0148688 A1 | 5/2014 | Ludwin et al. |

* cited by examiner

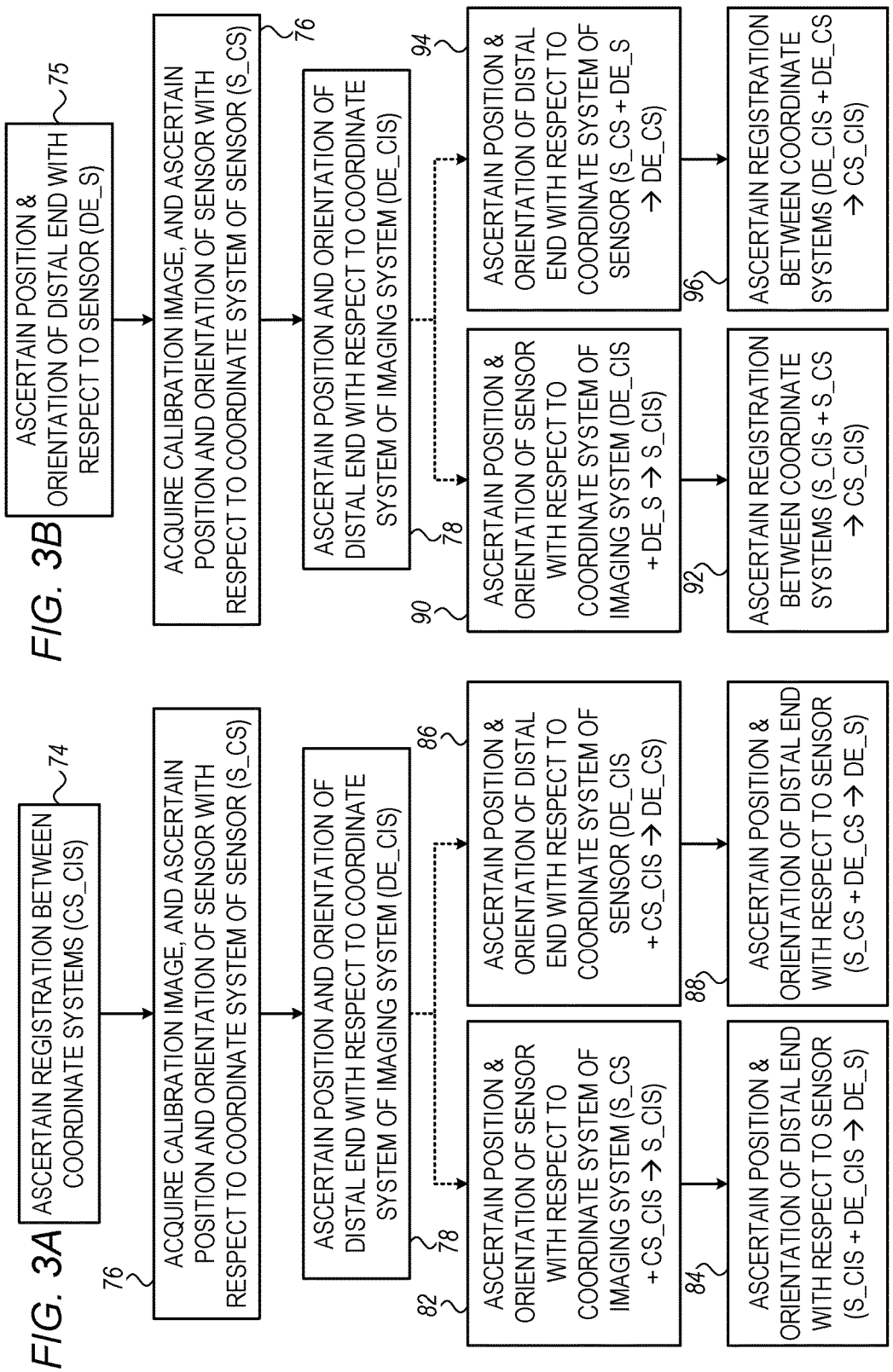

ASCERTAINING A POSITION AND ORIENTATION FOR VISUALIZING A TOOL

CROSS-REFERENCE TO RELATED APPLICATIONS

The present application is related to a US patent application entitled "Registration between coordinate systems for visualizing a tool," U.S. Ser. No. 14/978,864, filed on even date herewith.

FIELD OF THE INVENTION

Embodiments of the present invention relate to medical procedures, for example, those that involve mapping and/or ablation of cardiac tissue.

BACKGROUND

US Patent Publication 2014/0148688, whose disclosure is incorporated herein by reference, describes an invasive medical probe that includes an insertion tube, having a proximal end and a distal end configured for insertion into a body of a patient. Multiple arms extend distally from the distal end of the insertion tube. Each arm has a distal tip and includes a magnetic transducer and an adhesive element, which is configured to removably attach the distal tip to a tissue surface within the body.

U.S. Pat. No. 6,368,285, whose disclosure is incorporated herein by reference, describes a method for intracardially mapping a condition such as an electrical or mechanical property of a chamber of a heart. The method uses a catheter having a distal tip and at least one condition sensor contained therein or proximate thereto. The at least one sensor is capable of sensing condition information in the chamber and provides the three-dimensional position of the catheter tip in a positional frame of reference. The method includes the steps of acquiring first and second images of the chamber. The images are acquired from different projections and contain topological information of the chamber. The chamber images are registered with the positional frame of reference. The catheter distal tip is advanced into the catheter and is navigated to acquisition points under the guidance of topological information contained in or derived from the images. Condition and position information are acquired at each of the acquisition points, the points being sufficient in number and spacing to permit the generation of a map of the condition in the chamber. The topological information used to guide the navigation of the catheter is preferably a three-dimensional reconstruction of the chamber derived from the topological information contained in the images.

U.S. Pat. No. 7,937,132, whose disclosure is incorporated herein by reference, discloses a method and apparatus to deliver medical devices to targeted locations within human tissues using imaging data. The method enables the target location to be obtained from one imaging system, followed by the use of a second imaging system to verify the final position of the device. In particular, the invention discloses a method based on the initial identification of tissue targets using MR imaging, followed by the use of ultrasound imaging to verify and monitor accurate needle positioning. The invention can be used for acquiring biopsy samples to determine the grade and stage of cancer in various tissues including the brain, breast, abdomen, spine, liver, and kidney. The method is also useful for delivery of markers to a specific site to facilitate surgical removal of diseased tissue, or for the targeted delivery of applicators that destroy diseased tissues in-situ.

U.S. Pat. No. 7,653,426, whose disclosure is incorporated herein by reference, describes an endoscope-like image taking method that includes providing at least one peculiar index, which can be discriminated from other portions on an MR image, at the tip of a catheter, previously inserting a metal guide wire for guiding the catheter into a body cavity of a patient inserting the catheter into the body cavity along the guide wire, executing an MR imaging sequence of a plurality of sliced images intersecting the guide wire, reconstructing three-dimensional image data based upon the nuclear magnetic resonance signals, which are received by the guide wire, and determining the tip position and the inserting direction of the catheter by detecting the peculiar index provided at the tip of the catheter based upon the three-dimensional image data, and reconstructing the center projected image using the three-dimensional image data and setting the tip position and the inserting direction of the catheter as a view point and a line-of-sight direction and displaying the center projected image on a display means.

U.S. Pat. No. 8,974,460, whose disclosure is incorporated herein by reference, concerns a device for adjusting the position of a screw that is able to move a part of a surgical instrument, said device comprising: —a stem comprising a tip suited to the head of the screw, —an actuated system for driving said stem in rotation, —communication means to communicate with a control unit, such that the control unit transmits to the actuated system the number of turns to apply to the stem to reach the target position of the screw. The invention also concerns a surgical system for alignment of surgical guide means, comprising: —a positioning unit comprising a fixed part and a mobile part supporting the surgical guide means, the position of said mobile part being adjustable with respect to the fixed part by screws, —a referencing unit for detecting the position of the positioning unit with respect to a target position of the surgical guide means, —a control unit for computing the target position of screws, —said device for adjusting the positions of the screws.

US Patent Publication 2013/0083988, whose disclosure is incorporated herein by reference, describes a method for device visualization that includes receiving a set of physical characteristics including a description of spatial relationships of a plurality of markers within a device. Radiographic data of the device within a subject is acquired. An approximate location of each of the plurality of markers is identified within the radiographic data. A trajectory function is constructed for the device within the subject based on the identified approximate locations of each of the markers and the received set of physical characteristics. A section function is constructed for the device based on the set of physical characteristics and a 3D model is generated for the device based on the constructed trajectory function and the section function. A rendering of the 3D model is displayed on a display device.

US Patent Publication 2011/0230758, whose disclosure is incorporated herein by reference, describes a method and system for determining the current position of a selected portion of a medical catheter inserted into a tubular organ of the body of a patient, the method comprising the procedures of inserting a medical positioning system (MPS) catheter into the tubular organ, acquiring a plurality of mapping positions within the tubular organ, displaying a mapping position representation of the mapping positions, constructing a mapping path according to the mapping positions, inserting the medical catheter into the tubular organ until the selected portion reaches the initial position, displaying an operational image of the tubular organ, a path representation of the mapping path, and an initial position representation of the initial position superimposed on the operational image, registering the selected portion with the initial position, measuring a traveled length of the medical catheter within the tubular organ from the initial position, and estimating the current position.

SUMMARY OF THE INVENTION

There is provided, in accordance with some embodiments of the present invention, a method for coordinate-system registration. While a catheter that includes (i) a catheter body, and (ii) a catheter shaft, which includes a sensor and which is disposed inside a lumen of the catheter body, is inside a body of a subject, the coordinate system of the sensor is registered with the coordinate system of an imaging system. The registration uses (a) a calibration image, acquired by the imaging system, that shows an indication of a distal end of the catheter body, and (b) a signal from the sensor, but does not use any indication of the sensor shown in the calibration image. Using the registering, a visual output is generated.

In some embodiments, generating the visual output includes superimposing a visual representation of the distal end of the catheter body on an image of a portion of the body of the subject.

In some embodiments, the visual representation of the distal end of the catheter body includes a computer-generated model of the distal end of the catheter body.

In some embodiments, the distal end of the catheter body includes one or more electrodes, and the visual representation of the distal end of the catheter body includes a visual representation of the one or more electrodes.

In some embodiments, superimposing the visual representation of the distal end of the catheter body on the image of the portion of the body of the subject includes superimposing the visual representation of the distal end of the catheter body on the image of the portion of the body of the subject during an ablation of the portion of the body of the subject.

In some embodiments, generating the visual output includes displaying a map of a portion of the body of the subject.

In some embodiments, the map includes an electroanatomical map of at least a portion of a heart of the subject.

In some embodiments, the sensor is an electromagnetic sensor.

In some embodiments, the calibration image is a magnetic resonance imaging (MRI) image.

In some embodiments, the indication of the distal end of the catheter body includes a void in the MRI image that corresponds to the distal end of the catheter body.

In some embodiments, registering the coordinate system of the sensor with the coordinate system of the imaging system includes:

ascertaining a position and an orientation of the distal end of the catheter body with respect to the coordinate system of the imaging system, by identifying the indication of the distal end of the catheter body in the calibration image, based on the signal from the sensor, ascertaining a position and an orientation of the sensor with respect to the coordinate system of the sensor, and using (i) the ascertained position and orientation of the distal end of the catheter body with respect to the coordinate system of the imaging system, (ii) the ascertained position and orientation of the sensor with respect to the coordinate system of the sensor, and (iii) a known position and orientation of the distal end of the catheter body with respect to the sensor, registering the coordinate system of the sensor with the coordinate system of the imaging system.

There is further provided, in accordance with some embodiments of the present invention, apparatus that includes an electrical interface and a processor. While a catheter that includes (i) a catheter body, and (ii) a catheter shaft, which includes a sensor and which is disposed inside a lumen of the catheter body, is inside a body of a subject, the processor registers a coordinate system of the sensor with a coordinate system of an imaging system, using (a) a calibration image, acquired by the imaging system, that shows an indication of a distal end of the catheter body, and (b) a signal from the sensor received via the electrical interface, but not using any indication of the sensor shown in the calibration image. Using the registering, the processor drives a display to generate a visual output.

There is further provided, in accordance with some embodiments of the present invention, a computer software product including a tangible non-transitory computer-readable medium in which program instructions are stored. The instructions, when read by a processor, cause the processor to, while a catheter that includes (i) a catheter body, and (ii) a catheter shaft, which includes a sensor and which is disposed inside a lumen of the catheter body, is inside a body of a subject, register a coordinate system of the sensor with a coordinate system of an imaging system, using (a) a calibration image, acquired by the imaging system, that shows an indication of a distal end of the catheter body, and (b) a signal from the sensor, but not using any indication of the sensor shown in the calibration image. The instructions further cause the processor to, using the registering, drive a display to generate a visual output.

There is further provided, in accordance with some embodiments of the present invention, a method for ascertaining a position and an orientation of a distal end of a catheter body with respect to a sensor. While a catheter that includes (i) a catheter body, and (ii) a catheter shaft, which includes the sensor and which is disposed inside a lumen of the catheter body, is inside a body of a subject, the position and orientation are ascertained, based on (a) a calibration image, acquired by an imaging system, that shows an indication of the distal end of the catheter body, and (b) a signal from the sensor, but not based on any indication of the sensor shown in the calibration image. Using the ascertained position and orientation of the distal end of the catheter body with respect to the sensor, a visual output is generated.

In some embodiments, generating the visual output includes superimposing a visual representation of the distal end of the catheter body on an image of a portion of the body of the subject.

In some embodiments, the visual representation of the distal end of the catheter body includes a computer-generated model of the distal end of the catheter body.

In some embodiments, the distal end of the catheter body includes one or more electrodes, and the visual representation of the distal end of the catheter body includes a visual representation of the one or more electrodes.

In some embodiments, superimposing the visual representation of the distal end of the catheter body on the image of the portion of the body of the subject includes superimposing the visual representation of the distal end of the catheter body on the image of the portion of the body of the subject during an ablation of the portion of the body of the subject.

In some embodiments, generating the visual output includes displaying a map of a portion of the body of the subject.

In some embodiments, the map includes an electroanatomical map of at least a portion of a heart of the subject.

In some embodiments, the sensor is an electromagnetic sensor.

In some embodiments, the calibration image is a magnetic resonance imaging (MRI) image.

In some embodiments, the indication of the distal end of the catheter body includes a void in the MRI image that corresponds to the distal end of the catheter body.

In some embodiments, ascertaining the position and orientation of the distal end of the catheter body with respect to the sensor includes:

ascertaining a position and an orientation of the distal end of the catheter body with respect to a coordinate system of the imaging system, by identifying the indication of the distal end of the catheter body in the calibration image, based on the signal from the sensor, ascertaining a position and an orientation of the sensor with respect to the coordinate system of the sensor, and based on (i) the ascertained position and orientation of the distal end of the catheter body with respect to the coordinate system of the imaging system, (ii) the ascertained position and orientation of the sensor with respect to the coordinate system of the sensor, and (iii) a prior registration between the coordinate system of the sensor and the coordinate system of the imaging system, ascertaining the position and orientation of the distal end of the catheter body with respect to the sensor.

There is further provided, in accordance with some embodiments of the present invention, a catheter. The catheter includes a catheter body, shaped to define a lumen thereof, a distal end of the catheter body comprising one or more electrodes. The catheter further includes a catheter shaft that includes an electromagnetic sensor and is configured to be placed inside the lumen of the catheter body.

There is further provided, in accordance with some embodiments of the present invention, apparatus that includes an electrical interface and a processor. While a catheter that includes (i) a catheter body, and (ii) a catheter shaft, which includes a sensor and which is disposed inside a lumen of the catheter body, is inside a body of a subject, the processor ascertains a position and an orientation of a distal end of the catheter body with respect to the sensor, based on (a) a calibration image, acquired by an imaging system, that shows an indication of the distal end of the catheter body, and (b) a signal from the sensor, but not based on any indication of the sensor shown in the calibration image. Using the ascertained position and orientation of the distal end of the catheter body with respect to the sensor, the processor drives a display to generate a visual output.

There is further provided, in accordance with some embodiments of the present invention, a computer software product including a tangible non-transitory computer-readable medium in which program instructions are stored. The instructions, when read by a processor, cause the processor to, while a catheter that includes (i) a catheter body, and (ii) a catheter shaft, which includes a sensor and which is disposed inside a lumen of the catheter body, is inside a body of a subject, ascertain a position and an orientation of a distal end of the catheter body with respect to the sensor, based on (a) a calibration image, acquired by an imaging system, that shows an indication of the distal end of the catheter body, and (b) a signal from the sensor, but not based on any indication of the sensor shown in the calibration image. The instructions further cause the processor to, using the ascertained position and orientation of the distal end of the catheter body with respect to the sensor, drive a display to generate a visual output.

The present invention will be more fully understood from the following detailed description of embodiments thereof, taken together with the drawings, in which:

BRIEF DESCRIPTION OF THE DRAWINGS

FIGS. 3A-B are respective flow diagrams for calibration methods, practiced in accordance with some embodiments of the present invention;

DETAILED DESCRIPTION OF EMBODIMENTS

Overview

Figure 1:
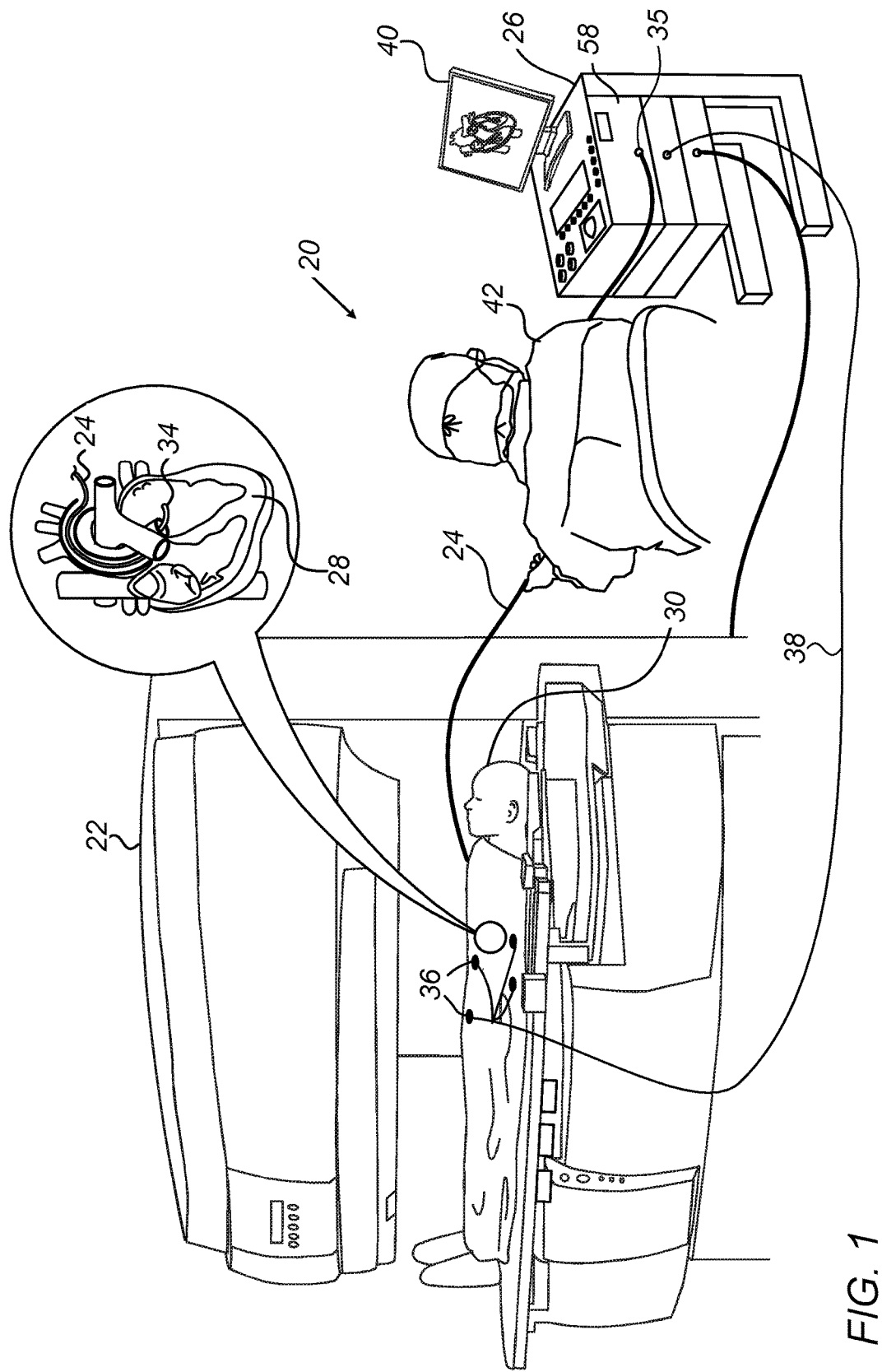
FIG. 1 is a schematic illustration of a system for mapping and/or ablation of cardiac tissue, in accordance with some embodiments of the present invention.

Embodiments of the present invention provide a catheter for use for anatomical or electroanatomical mapping, and/or for ablation. In addition to electrodes for mapping and/or ablation, the catheter includes an electromagnetic sensor, which is used for navigating the catheter within the body of a subject. Typically, an external magnetic system induces a voltage and/or current in the sensor. The induced voltage and/or current in the sensor is measured, and is then used to derive the position and orientation of the sensor. Alternatively, the sensor may induce a voltage and/or current in the external magnetic system. The induced voltage and/or current in the external magnetic system is measured, and is then used to derive the position and orientation of the sensor.

References in the present application, including in the claims, to a "signal," or "tracking signal," from the sensor, refer to the above-described voltage and/or current induced in the sensor or in the external magnetic system. The external magnetic system, the sensor, and any other associated components (e.g., hardware and/or software components, such as the processor described below) are collectively referred to herein as a "tracking system."

In embodiments of the present invention, the catheter comprises two separate components; one component, an inner shaft of the catheter, comprises the electromagnetic sensor and its associated circuitry, while the other component, a hollow outer body of the catheter, comprises the mapping and/or ablation electrodes, which are coupled to the distal end of the catheter body. The catheter shaft is inserted into the lumen of the catheter body, and both components are then inserted into the subject.

Typically, since the catheter shaft is covered by the catheter body, only the catheter body needs to be discarded after the procedure, while the catheter shaft—which includes relatively expensive components—may be reused. Hence, the "two-piece catheter" embodiments of the present invention provide significant cost savings, relative to conventional "one-piece catheters" that include similar sensors. (The electrodes, as opposed to the sensor, need to touch the tissue, and therefore, the electrodes need to be positioned on the catheter body. In any case, since the electrodes are typically relatively inexpensive, there is typically no significant loss in discarding the catheter body after the procedure.)

Embodiments of the present invention also provide methods and apparatus for navigating the catheter during the mapping or ablation procedure, using the signal from the sensor. For example, during an electroanatomical mapping of the heart, a computer-generated model of the distal end of the catheter body, which includes the mapping electrodes, may be superimposed on an image of the subject's heart, at the location, and with the orientation, indicated by the signal from the sensor.

In order to properly display the model of the distal end of the catheter body in the image, the following two challenges need to be overcome:

(a) The coordinate system of the imaging system used to acquire the image needs to be registered with the coordinate system of the sensor.

(b) The position and orientation of the distal end of the catheter body relative to the sensor needs to be ascertained. (This challenge is amplified by the fact that, as described above, the sensor is not disposed on the catheter body, and hence, there is greater variance in the positional and orientational offset between the catheter body and the sensor.)

Embodiments of the present invention address both of the above challenges, thus allowing the model of the distal end of the catheter body to be properly displayed. In some embodiments, a pre-procedural registration between the coordinate systems is performed, e.g., using fiducials. (This addresses the first challenge.) Subsequently, a calibration image that shows an indication of the distal end of the catheter body is acquired, and the calibration image is used to ascertain the position and orientation of the distal end of the catheter body with respect to the coordinate system of the imaging system. Using this information, the sensor signal, and the pre-procedural registration between the coordinate systems (but not using any indication of the sensor in the calibration image—which, in any case, typically does not show the sensor at all), the position and orientation of the distal end of the catheter body relative to the sensor is ascertained. (This addresses the second challenge.)

In other embodiments, a pre-procedural calibration procedure is performed, to ascertain the position and orientation of the distal end of the catheter body relative to the sensor. (This addresses the second challenge.) Subsequently, a calibration image that shows an indication of the distal end of the catheter body is acquired, and the calibration image is used to ascertain the position and orientation of the distal end of the catheter body with respect to the coordinate system of the imaging system. Using this information, the sensor signal, and the known position and orientation of the distal end of the catheter body relative to the sensor (but not using any indication of the sensor in the calibration image—which, in any case, typically does not show the sensor at all), the two coordinate systems are registered with one another. (This addresses the first challenge.)

Typically, magnetic resonance imaging (MRI) is used to acquire the calibration image, along with any subsequent images of the subject's anatomy. The MRI system communicates bi-directionally with the tracking system, such that, for example, the tracking system may instruct the MRI system to acquire an MRI "slice" at a particular position and orientation related to the current position and orientation of the sensor.

In the MRI images, the distal end of the catheter body typically appears as a void. Hence, the position and orientation of the distal end of the catheter body with respect to the coordinate system of the MRI imaging system may be ascertained, by identifying the void in the image.

System Description

Figure 2:
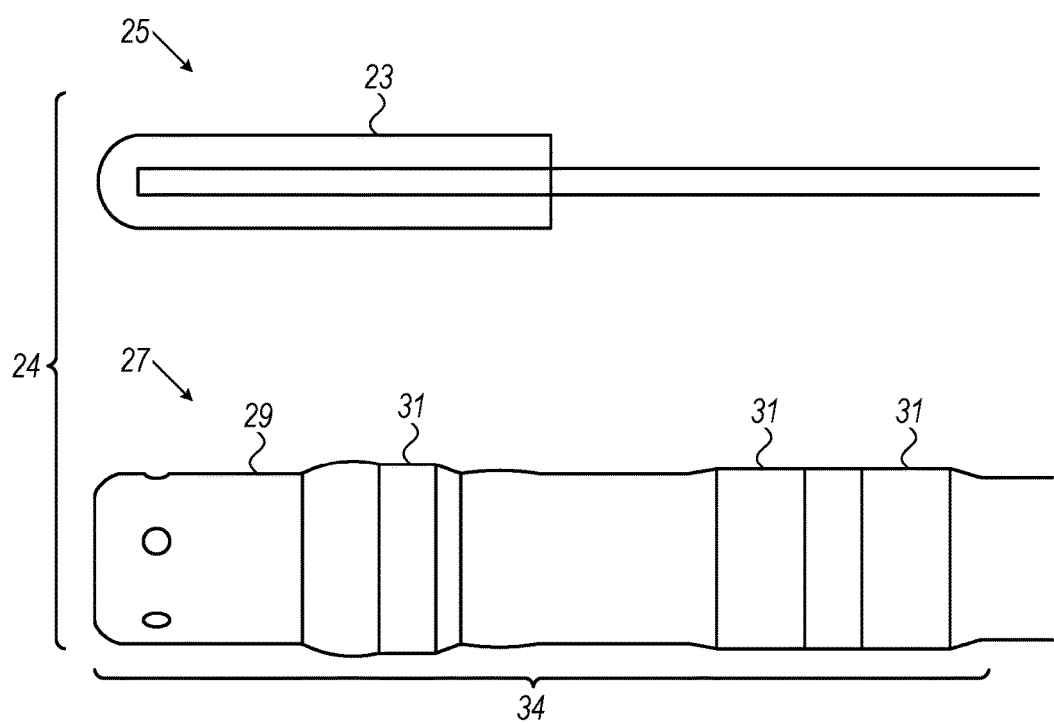
FIG. 2 is a schematic illustration of a distal portion of a catheter, in accordance with some embodiments of the present invention.

Reference is initially made to FIG. 1, which is a schematic illustration of a system 20 for mapping and/or ablation of cardiac tissue, in accordance with some embodiments of the present invention. Reference is additionally made to FIG. 2, which is a schematic illustration of a distal portion of a catheter 24, in accordance with some embodiments of the present invention.

System 20 comprises (i) an imaging system, such as an MRI scanner 22, (ii) a catheter 24, and (iii) a control console 26. Catheter 24 comprises a catheter body 27, which comprises a distal end 34 that typically comprises one or more electrodes. For example, in some embodiments, distal end 34 comprises at least one ablation electrode 29, and one or more mapping electrodes 31. Catheter 24 further comprises a catheter shaft 25, which comprises a sensor, such as an electromagnetic sensor 23. Catheter body 27 is shaped to define a lumen, into which catheter shaft 25 is inserted prior to the catheter being inserted into the subject. (In FIG. 2, for clarity, catheter shaft 25 is shown alongside catheter body 27, rather than inside the catheter body, as would be the case during a procedure.) As described above, the placement of sensor 23 and its associated circuitry on the unexposed catheter shaft, rather than on the exposed outer portion of the catheter, typically provides significant cost savings.

As depicted in FIG. 1, a physician 42 inserts catheter 24 through the vascular system of a subject 30 so that distal end 34 of the catheter body enters a body cavity, herein assumed to be a chamber of the subject's heart 28. As described above, sensor 23 provides a tracking signal that facilitates the navigation of the catheter. In some embodiments, the sensor is an electromagnetic sensor, and electromagnetic tracking techniques are used, for example, as described in U.S. Pat. Nos. 5,391,199, 5,443,489, 6,788,967, 6,690,963, 5,558,091, 6,172,499, and 6,177,792, whose disclosures are incorporated herein by reference. In other embodiments, other tracking techniques are used, such as the impedance-based tracking techniques described in U.S. Pat. Nos. 5,983,126, 6,456,864 and 5,944,022, whose disclosures are also incorporated herein by reference.

Upon the distal end of the catheter entering the cardiac chamber, mapping electrodes 31 may be used for acquiring intracardiac electrocardiogram (ECG) signals that allow the chamber of the heart to be electroanatomically mapped. The intracardiac ECG signals acquired by the mapping electrodes are transferred, typically by conductors and/or optical fibers in catheter 24, to a control console 26, where the signals are analyzed. Alternatively or additionally, ablation electrode 29 may be used for performing cardiac ablation.

Alternatively or additionally to acquiring intracardiac ECG signals using catheter 24, system 20 may acquire body-surface ECG signals from the skin of subject 30, typically via a number of conductive patches 36, which act as electrodes, on the skin of the subject. The body-surface ECG signals are conveyed via a cable 38 to control console 26.

Control console 26 comprises a processor 58. Processor 58 receives, via an electrical interface 35, the tracking signals from the sensor. The processor further receives the data acquired by MRI scanner 22, and/or any acquired intracardiac or body-surface ECG signals. As described in detail hereinbelow, processor 58 processes the received data, and, in response thereto, drives a display 40 to display relevant visual output, and/or generates other appropriate output.

In general, processor 58 may be embodied as a single processor, or a cooperatively networked or clustered set of processors. Processor 58 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Reference is now made to FIGS. 3A-B, which are respective flow diagrams for calibration methods, practiced in accordance with some embodiments of the present invention.

By way of introduction, the calibration method of FIG. 3A differs from that of FIG. 3B in that the variable that is ascertained at the beginning of the method of FIG. 3A is ascertained at the end of the method of FIG. 3B, and vice versa. In particular:

(i) The calibration method of FIG. 3A begins with a registration step 74, at which a (typically isometric) registration between the coordinate system of the imaging system, CIS, and the coordinate system of the sensor, CS, is performed, e.g., using fiducials. The resulting registration, CS_CIS, is then used to ascertain DE_S, which is the position and orientation of the distal end of the catheter body with respect to the sensor that is located inside the lumen of the catheter body.

(ii) The calibration method of FIG. 3B begins with a first calibration step 75, at which the position and orientation of the distal end of the catheter body with respect to the sensor, DE_S, is ascertained, e.g., using specialized calibration equipment. DE_S is then used to ascertain CS_CIS, which is the registration between the coordinate system of the imaging system and the coordinate system of the sensor.

In summary, in FIG. 3A, CS_CIS is used to ascertain DE_S, while in FIG. 3B, the opposite is the case: DE_S is used to ascertain CS_CIS.

The description below will now continue to describe the calibration methods of FIGS. 3A-B, with reference being additionally made to FIG. 4A, which is a schematic illustration of a calibration image 60, acquired in accordance with some embodiments of the present invention. (Although, for ease of illustration, calibration image 60 is depicted in FIG. 4A as a two-dimensional image, it is noted that the calibration image is typically three-dimensional.)

Subsequently to the insertion of catheter 24 into the body of the subject, calibration image 60 is acquired, at a calibration-image-acquiring step 76. For example, FIG. 4A depicts a scenario in which the calibration image is acquired upon catheter 24 reaching heart 28 of the subject. In FIG. 4A, blood within the chambers 33 of the heart is shown in white, indicating that the blood is visible to the MRI scanner. Conversely, surrounding tissue is shown in a darker shade, indicating that this tissue is less visible to the MRI scanner, due to having a lower concentration of water than does the blood. (It is noted that FIG. 4A is based on data from a phantom, and hence, the anatomical details therein do not correspond exactly to actual human anatomy.)

In calibration-image-acquiring step 76, the position and orientation of the sensor in the calibration image is also ascertained, based on the signal from the sensor. The sensor signal naturally provides the position and orientation of the sensor with respect to the coordinate system of the sensor (which may also be referred to as the coordinate system of the tracking system), S_CS. (Typically, the sensor is not shown in the calibration image, such that the position and orientation of the sensor relative to the coordinate system of the imaging system is not ascertainable solely from the calibration image.)

Subsequently, at a DE_CIS-ascertaining step 78, the calibration image is used to ascertain the position and orientation of the distal end of the catheter body with respect to the coordinate system of the imaging system (DE_CIS). For example, if MRI scanner 22 is the imaging system in use, distal end 34 of the catheter body will typically be indicated in the calibration image by a void 62, since the catheter is typically made of MRI-invisible material. Hence, by identifying void 62, the position and orientation of the distal end of the catheter body with respect to the coordinate system of the MRI scanner may be ascertained. In some embodiments, processor 58 automatically identifies the void using image-processing techniques.

In the calibration method of FIG. 3A, processor 58 then ascertains the position and orientation of the distal end of the catheter body with respect to the sensor, DE_S. As indicated by the dotted arrows in the flow diagram, DE_S may be ascertained in either one of the following ways:

(i) In some embodiments, the processor, at a S_CIS-ascertaining step 82, ascertains the position and orientation of the sensor with respect to the coordinate system of the imaging system, S_CIS, using the known registration between the two coordinate systems (S_CS+CS_CIS→S_CIS). Then, at a DE_S-ascertaining step 84, the processor ascertains the position and orientation of the distal end of the catheter body with respect to the sensor, DE_S, using the known position and orientation of both the sensor and the distal end of the catheter body with respect to the coordinate system of the imaging system (S_CIS+DE_CIS→DE_S).

(ii) In other embodiments, the processor, at a DE_CS-ascertaining step 86, ascertains the position and orientation of the distal end of the catheter body with respect to the coordinate system of the sensor, DE_CS, using the known registration between the two coordinate systems (DE_CIS+CS_CIS→DE_CS). Then, at an alternate DE_S-ascertaining step 88, the processor ascertains the position and orientation of the distal end of the catheter body with respect to the sensor, DE_S, using the known coordinates of both the sensor and the distal end of the catheter body with respect to the coordinate system of the sensor (S_CS+DE_CS→DE_S).

In the calibration method of FIG. 3B, on the other hand, DE_S, which is known from first calibration step 75, is used to ascertain CS_CIS. As indicated by the dotted arrows in the flow diagram, CS_CIS may be ascertained in either one of the following ways:

(i) In some embodiments, the processor, at an alternate S_CIS-ascertaining step 90, ascertains the position and orientation of the sensor with respect to the coordinate system of the imaging system, S_CIS, using the known positional and orientational offset between the sensor and the distal end of the catheter body (DE_CIS+DE_S→S_CIS). Then, at a CS_CIS-ascertaining step 92, the processor ascertains the registration between the two coordinate systems, CS_CIS, using the known position and orientation of the sensor with respect to both of the coordinate systems (S_CIS+SCS→CS_CIS).

(ii) In other embodiments, the processor, at an alternate DE_CS-ascertaining step 94, ascertains the position and orientation of the distal end of the catheter body with respect to the coordinate system of the sensor, DE_CS, using the known positional and orientational offset between the sensor and the distal end of the catheter body (S_CS+DE_S→DE_CS). Then, at an alternate CS_CIS-ascertaining step 96, the processor ascertains the registration between the two coordinate systems, CS_CIS, using the known position and orientation of the distal end of the catheter body with respect to both of the coordinate systems (DE_CIS+DE_CS→C-S_CIS).

As further described below with reference to FIGS. 3C and 4B, the processor uses the information acquired during calibration to facilitate an anatomical or electroanatomical mapping of the subject's heart, and/or the performance of another procedure, such as a cardiac ablation.

Figure 3C:
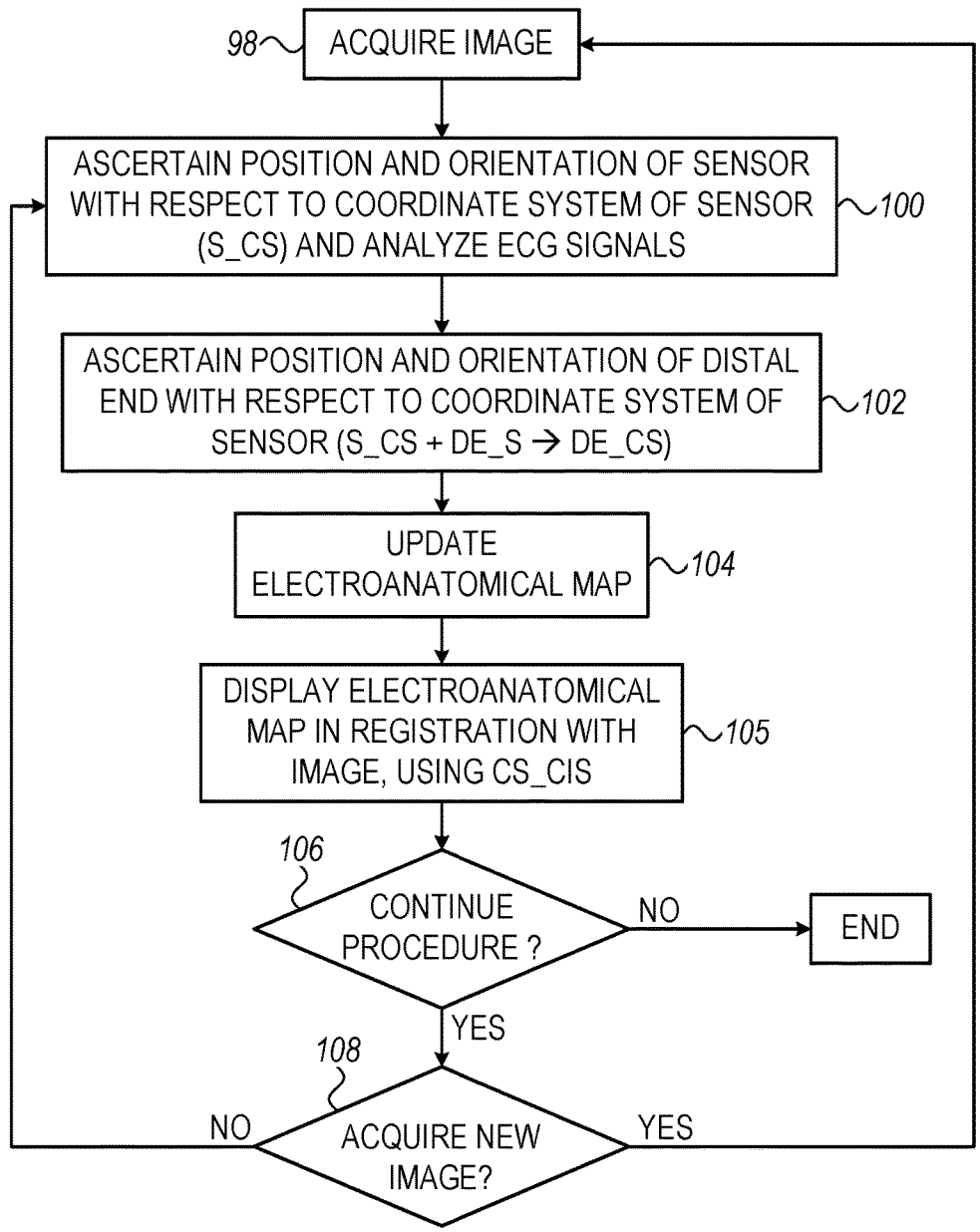
FIG. 3C is a flow diagram for a method for updating a display during a procedure, in accordance with some embodiments of the present invention.
Figure 4A:
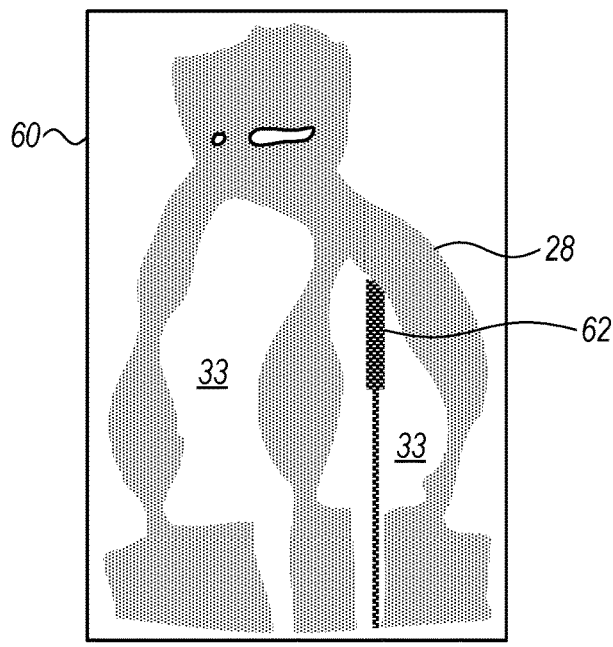
FIG. 4A is a schematic illustration of a calibration image, acquired in accordance with some embodiments of the present invention.

Reference is now made to FIG. 3C, which is a flow diagram for an electroanatomical mapping procedure, in accordance with some embodiments of the present invention. Reference is additionally made to FIG. 4B, which is an example of a visual output 63, including a three-dimensional electroanatomical map 68, displayed on display 40 (FIG. 1), in accordance with some embodiments of the present invention.

First, at an image-acquiring step 98, an image 72 of the relevant portion of the subject's body is acquired. For example, when performing an electroanatomical mapping of a surface of the subject's heart, an image of the surface may be acquired at image-acquiring step 98. (In some cases, if calibration image 60 already shows the relevant portion of the subject's body, image-acquiring step 98 may be omitted. Stated differently, in some cases, calibration image 60 is not used solely for calibration, but rather, is also used in real-time, while the actual mapping or ablation takes place.) The acquired image is then displayed in visual output 63.

Subsequently, as the physician moves the catheter along the surface of the subject's heart, electrodes 31 record intracardiac ECG signals, and the processor repeatedly performs the following sequence of steps:

(i) At a data-acquiring step 100, the processor receives and analyzes the ECG signals, and also ascertains the position and orientation of the sensor, SCS, at the time that the ECG signals were recorded, based on the sensor signal.

(ii) At a real-time-DE_CS-ascertaining step 102, the processor uses DE_S, obtained during calibration, to ascertain from S_CS the position and orientation of the distal end of the catheter, DE_CS.

(iii) At a map-updating step 104, the processor updates electroanatomical map 68. For example, the processor may derive various local activation times from the ECG signals, and update the electroanatomical map to reflect these local activation times. In performing this updating, the processor uses DE_CS to derive the positions of the electrodes on the tissue. Typically, in updating the map, the processor also places a visual representation of the distal end of the catheter body on the electroanatomical map, at the position and orientation indicated by DE_CS.

(iv) At a displaying step 105, the processor displays the updated electroanatomical map in registration with image 72, using CS_CIS, which was obtained during calibration. For example, as shown in FIG. 4B, the electroanatomical map may be overlaid on image 72 in visual output 63. Effectively, by displaying the map in registration with the image, the processor superimposes the visual representation of the distal end of the catheter body over the image. Hence, the physician is able to readily see the current position and orientation of the distal end of the catheter body with respect to the subject's anatomy.

Figure 4B:
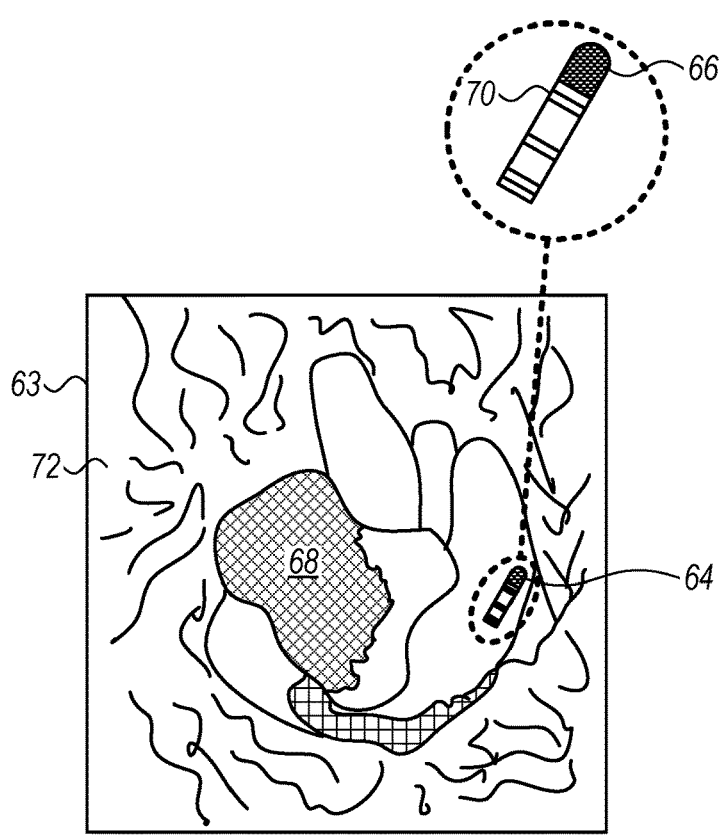
FIG. 4B is an example of visual output displayed on a display, in accordance with some embodiments of the present invention.

FIG. 4B shows visual output 63 as it may appear following displaying step 105. The white portions of the heart shown in visual output 63 correspond to portions of the heart that have not yet been electroanatomically mapped. Conversely, the colored portions of the map—indicated in FIG. 4B by various patterns of shading—correspond to those portions of the heart have been electroanatomically mapped. The various colors correspond, for example, to the various local activation times at different portions of the heart, these times being derived from the ECG signals, as described above.

At any point, the physician may decide, at a first decision step 106, to end the procedure. The physician may also decide, at a second decision step 108, to acquire a new image.

Typically, the visual representation of the distal end of the catheter body is a computer-generated model 64. Typically, model 64 includes a visual representation of the electrodes that are coupled to the distal end of the catheter body, including, for example, a visual representation 70 of mapping electrodes 31, and/or a visual representation 66 of ablation electrode 29.

In some embodiments, image 72 is not acquired, and the electroanatomical map is therefore displayed at displaying step 105 without being overlaid on, or otherwise combined with, any other image.

The above-described techniques may also be applied to other types of procedures, mutatis mutandis. For example, during an ablation procedure, at data-acquiring step 100, the processor may receive and/or analyze information relating to the passing of an ablating current, and also ascertain the position and orientation of the sensor, S_CS, at the time of the passing of the ablating current. The processor may then ascertain DE_CS, as described above. At map-updating step 104, the processor may then update electroanatomical map 68 by adding markers to the map to mark the areas of tissue that were ablated, these areas being determined by using DE_CS to derive the position of the ablating electrode on the tissue. Alternatively or additionally, the processor may place a visual representation of the distal end of the catheter body on the electroanatomical map, as described above, to help guide the ablation procedure.

It is noted that, notwithstanding the specific MRI-based embodiments described herein, embodiments described herein may be practiced with any type of imaging system using any relevant imaging modality, regardless of whether the distal end of the catheter body appears "positively" or "negatively" in images that are acquired by the imaging system. Moreover, although the present description and figures relate mainly to cardiac procedures, it is noted that apparatus and methods described herein may be applied to other types of procedures, such as Ear, Nose & Throat (ENT) or pulmonary procedures.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   providing an electrical interface;
   providing a processor; and
   while a catheter that includes (i) a catheter body, and (ii) a catheter shaft, which includes a sensor and which is disposed inside a lumen of the catheter body, is inside a body of a subject, ascertaining a position and an orientation of a distal end of the catheter body with respect to the sensor, based on (a) a calibration image, acquired by an imaging system, that shows an indication of the distal end of the catheter body, and (b) a signal from the sensor, but not based on any indication of the sensor shown in the calibration image; and
   using the position and orientation of the distal end of the catheter body with respect to the sensor, generating a visual output,
   wherein generating the visual output comprises displaying a map of a portion of the body of the subject,
   wherein the map includes an electroanatomical map of at least a portion of a heart of the subject,
   wherein the calibration image is an MRI image,
   wherein the indication of the distal end of the catheter body includes a void in the MRI image that corresponds to the distal end of the catheter body,
   wherein ascertaining the position and orientation of the distal end of the catheter body with respect to the sensor comprises:
      ascertaining a position and an orientation of the distal end of the catheter body with respect to a coordinate system of the imaging system, by identifying the indication of the distal end of the catheter body in the calibration image,
      based on the signal from the sensor, ascertaining a position and an orientation of the sensor with respect to the coordinate system of the sensor, and
      based on (i) the position and orientation of the distal end of the catheter body with respect to the coordinate system of the imaging system, (ii) the position and orientation of the sensor with respect to the coordinate system of the sensor, and (iii) a prior registration between the coordinate system of the sensor and the coordinate system of the imaging system, ascertaining the position and orientation of the distal end of the catheter body with respect to the sensor,
   further comprising performing the following steps,
      receiving and analyzing a plurality of ECG signals, and wherein the processor ascertains the position and orientation of the sensor at the time that the ECG signals were recorded, based on the sensor signal,
      using DE_S, wherein DE_S denotes position and orientation of the distal end of the catheter body with respect to the sensor obtained during calibration, to ascertain DE_CS, wherein DE_CS denotes position and orientation of the distal end of the catheter body with respect to the coordinate system of the sensor, from S_CS, wherein S_CS denotes position and orientation of the sensor with respect to the coordinate system of the sensor,
      updating the electroanatomical map, wherein the processor derives a plurality of local activation times from the ECG signals, and updates the electroanatomical map to reflect the local activation times, wherein, in performing the updating, the processor uses DE_CS to derive positions of the electrodes on tissue inside the body of the subject, wherein in updating the map, the processor places a visual representation of the distal end of the catheter body on the electroanatomical map, at the position and orientation indicated by DE_CS, and
      displaying the electroanatomical map in registration with the calibration image using CS_CIS, wherein CS_CIS denotes registration between the coordinate system of the imaging system.

2. The method according to claim 1, wherein generating the visual output comprises superimposing a visual representation of the distal end of the catheter body on an image of a portion of the body of the subject.

3. The method according to claim 2, wherein the distal end of the catheter body includes one or more electrodes, and wherein the visual representation of the distal end of the catheter body includes a visual representation of the one or more electrodes.

4. The method according to claim 2, wherein superimposing the visual representation of the distal end of the catheter body on the image of the portion of the body of the subject comprises superimposing the visual representation of the distal end of the catheter body on the image of the portion of the body of the subject during an ablation of the portion of the body of the subject.

5. The method according to claim 1, wherein the sensor is an electromagnetic sensor.

6. Apparatus, comprising:
   an electrical interface; and
   a processor, configured to: while a catheter that includes (i) a catheter body, and (ii) a catheter shaft, which includes a sensor and which is disposed inside a lumen of the catheter body, is inside a body of a subject, ascertain a position and an orientation of a distal end of the catheter body with respect to the sensor, based on (a) a calibration image, acquired by an imaging system, that shows an indication of the distal end of the catheter body, and (b) a signal from the sensor, but not based on any indication of the sensor shown in the calibration image; and
   using the position and orientation of the distal end of the catheter body with respect to the sensor, drive a display to generate a visual output,
   wherein the processor is configured to drive the display to generate the visual output by driving the display to display a map of a portion of the body of the subject,
   wherein the map includes an electroanatomical map of at least a portion of a heart of the subject, wherein the calibration image is an MRI image,
wherein the indication of the distal end of the catheter body includes a void in the MRI image that corresponds to the distal end of the catheter body,
wherein the processor is configured to ascertain the position and orientation of the distal end of the catheter body with respect to the sensor by:
  ascertaining a position and an orientation of the distal end of the catheter body with respect to a coordinate system of the imaging system, by identifying the indication of the distal end of the catheter body in the calibration image,
  based on the signal from the sensor, ascertaining a position and an orientation of the sensor with respect to the coordinate system of the sensor, and
  based on (i) the position and orientation of the distal end of the catheter body with respect to the coordinate system of the imaging system, (ii) the position and orientation of the sensor with respect to the coordinate system of the sensor, and (iii) a prior registration between the coordinate system of the sensor and the coordinate system of the imaging system, ascertaining the position and orientation of the distal end of the catheter body with respect to the sensor,
wherein the processor is further adapted to perform the following steps,
  receiving and analyzing a plurality of ECG signals, and wherein the processor ascertains the position and orientation of the sensor at the time that the ECG signals were recorded, based on the sensor signal,
  using DE_S, wherein DE_S denotes position and orientation of the distal end of the catheter body with respect to the sensor obtained during calibration, to ascertain DE_CS, wherein DE_CS denotes position and orientation of the distal end of the catheter body with respect to the coordinate system of the sensor, from S_CS, wherein S_CS denotes position and orientation of the sensor with respect to the coordinate system of the sensor,
  updating the electroanatomical map, wherein the processor derives a plurality of local activation times from the ECG signals, and updates the electroanatomical map to reflect the local activation times, wherein, in performing the updating, the processor uses DE_CS to derive positions of the electrodes on tissue inside the body of the subject, wherein in updating the map, the processor places a visual representation of the distal end of the catheter body on the electroanatomical map, at the position and orientation indicated by DE_CS, and
  displaying the electroanatomical map in registration with the calibration image using CS_CIS, wherein CS_CIS denotes registration between the coordinate system of the imaging system.

7. The apparatus according to claim 6, wherein the processor is configured to drive the display to generate the visual output by driving the display to superimpose a visual representation of the distal end of the catheter body on an image of a portion of the body of the subject.

8. The apparatus according to claim 7, wherein the distal end of the catheter body includes one or more electrodes, and wherein the visual representation of the distal end of the catheter body includes a visual representation of the one or more electrodes.

9. The apparatus according to claim 6, wherein the sensor is an electromagnetic sensor.

* * * * *